United States Patent
Bunnelle

(10) Patent No.: US 10,357,407 B2
(45) Date of Patent: *Jul. 23, 2019

(54) HOT MELT ADHESIVE

(71) Applicant: The Procter & Gamble Company, Cincinnati, OH (US)

(72) Inventor: William L. Bunnelle, Ham Lake, MN (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/574,701

(22) Filed: Dec. 18, 2014

(65) Prior Publication Data

US 2015/0174286 A1 Jun. 25, 2015

Related U.S. Application Data

(60) Provisional application No. 61/918,434, filed on Dec. 19, 2013.

(51) Int. Cl.
| | |
|---|---|
| *B32B 7/12* | (2006.01) |
| *C09J 5/06* | (2006.01) |
| *C08L 23/20* | (2006.01) |
| *C08L 23/22* | (2006.01) |
| *C09J 123/20* | (2006.01) |
| *C09J 123/22* | (2006.01) |
| *A61F 13/15* | (2006.01) |
| *A61L 15/24* | (2006.01) |
| *A61L 15/58* | (2006.01) |
| *B32B 23/00* | (2006.01) |
| *A61L 15/42* | (2006.01) |

(52) U.S. Cl.
CPC .. *A61F 13/15203* (2013.01); *A61F 13/15699* (2013.01); *A61L 15/24* (2013.01); *A61L 15/42* (2013.01); *A61L 15/585* (2013.01); *B32B 7/12* (2013.01); *B32B 23/00* (2013.01); *C08L 23/22* (2013.01); *C09J 5/06* (2013.01); *C09J 123/20* (2013.01); *C09J 123/22* (2013.01); *A61F 2013/15569* (2013.01); *A61L 2300/802* (2013.01); *B32B 2250/02* (2013.01); *B32B 2555/02* (2013.01); *C08L 2205/025* (2013.01); *C08L 2207/324* (2013.01); *C09J 2201/61* (2013.01); *Y10T 428/3188* (2015.04); *Y10T 428/31938* (2015.04)

(58) Field of Classification Search
CPC .... C08L 23/22; C08L 23/20; C08L 2205/025; C09J 123/22; C09J 123/20; C09J 2201/61; C09J 5/06; A61F 2013/15569; B32B 2555/02; B32B 7/12
See application file for complete search history.

(56) References Cited

U.S. PATENT DOCUMENTS

| | | |
|---|---|---|
| 3,338,992 A | 8/1967 | Allison |
| 3,341,394 A | 12/1967 | Allison |
| 3,502,538 A | 3/1970 | Petersen |
| 3,502,763 A | 3/1970 | Hartmann |
| 3,542,615 A | 11/1970 | Dobo et al. |
| 3,692,618 A | 9/1972 | Dorschner et al. |
| 3,802,817 A | 9/1974 | Matsuki et al. |
| 3,848,594 A | 11/1974 | Buell |
| 3,849,241 A | 11/1974 | Butin et al. |
| 3,860,003 A | 1/1975 | Buell |
| 3,900,361 A * | 8/1975 | Hoppe .................. C09J 123/20 156/334 |
| 4,046,945 A | 9/1977 | Baxmann et al. |
| 4,340,563 A | 7/1982 | Appel et al. |
| 4,610,678 A | 9/1986 | Weisman et al. |
| 4,662,875 A | 5/1987 | Hirotsu et al. |
| 4,673,402 A | 6/1987 | Weisman et al. |
| 4,699,622 A | 10/1987 | Toussant et al. |
| 4,761,450 A | 8/1988 | Lakshmanan et al. |
| 4,808,178 A | 2/1989 | Aziz et al. |
| 4,834,735 A | 5/1989 | Alemany et al. |
| 4,857,594 A | 8/1989 | Lakshmanan et al. |
| 4,846,815 A | 11/1989 | Scripps |
| 4,888,231 A | 12/1989 | Angstadt |
| 4,894,060 A | 1/1990 | Nestegard |
| 4,909,803 A | 3/1990 | Aziz et al. |
| 4,940,464 A | 7/1990 | VanGompel et al. |
| 4,946,527 A | 7/1990 | Battrell |
| 4,892,536 A | 9/1990 | Desmarais et al. |
| 4,963,140 A | 10/1990 | Robertson et al. |
| 4,990,147 A | 5/1991 | Freeland |
| 5,037,416 A | 6/1991 | Allen et al. |
| 5,092,861 A | 3/1992 | Nomura et al. |

(Continued)

FOREIGN PATENT DOCUMENTS

| | | |
|---|---|---|
| AU | 2013203866 | 12/2013 |
| CN | 1254361 | 5/2000 |

(Continued)

OTHER PUBLICATIONS

International Search Report and Written Opinion for PCT/US2014/071082, dated Feb. 26, 2015, 9 pages.
"Linxar™ 127 Polymer Data Sheet," ExxonMobil Chemical, Nov. 2010, 1 page.
"REXtac LLC, Advance Technology, Huntsman Rextac E-101," 1990, 2 pages.
"Vistamaxx™ 2330 Propylene-based Elastomer," ExxonMobil Chemical, Last updated: Jan. 26, 2011, http://prospector.ides.com/DataView.aspx?E=114449, 2 pages.
ExxonMobil Chemical, "Product datasheets for Vistamaxx™ propylene-based elastomers," Sep. 17, 2012, 1 page.
INEOS Oligomers, "Indopol Polybutene Product Data, Indopol Polybutene Grade: H-300," Sep. 17, 2012, 2 pages.
International Preliminary Report on Patentability for PCT/US2014/071082, dated Jun. 30, 2016, 8 pages.
Sustic, "New APAO Offer Expanded Properties for HMA Applications," *Adhesives Age*, Nov. 1992, 5 pages.
Sustic, "Novel Amorphous Polyalphaolefins (APAO) in Hot Melt Ashesive Formulations," *Hot Melt Symposium*,1991, pp. 193-200.

*Primary Examiner* — Peter S Vasat
(74) *Attorney, Agent, or Firm* — Andrew J. Hagerty

(57) ABSTRACT

A hot melt adhesive material and articles made using the hot melt adhesive to assemble structures in an article. The adhesive material typically is manufactured by blending amorphous polymer with a compatible amorphous polymer.

23 Claims, No Drawings

(56) References Cited

U.S. PATENT DOCUMENTS

| | | | |
|---|---|---|---|
| 5,147,345 A | 9/1992 | Young et al. |
| 5,151,092 A | 9/1992 | Buell et al. |
| 5,137,537 A | 11/1992 | Herron et al. |
| 5,213,881 A | 5/1993 | Timmons et al. |
| 5,217,812 A | 6/1993 | Lee |
| 5,221,274 A | 6/1993 | Buell et al. |
| 5,242,436 A | 7/1993 | Weil et al. |
| 5,246,433 A | 9/1993 | Bridges et al. |
| 5,260,345 A | 9/1993 | Desmarais et al. |
| 5,269,775 A | 12/1993 | Freeland et al. |
| 5,302,675 A | 4/1994 | Sustic et al. |
| 5,342,338 A | 8/1994 | Roe |
| 5,391,434 A | 2/1995 | Krutzel |
| 5,397,316 A | 3/1995 | Lavon et al. |
| 5,387,207 A | 7/1995 | Dyer et al. |
| 5,499,978 A | 3/1996 | Buell et al. |
| 5,580,411 A | 3/1996 | Nease et al. |
| 5,507,736 A | 4/1996 | Clear et al. |
| 5,571,096 A | 5/1996 | Dobrin et al. |
| 5,554,145 A | 10/1996 | Roe et al. |
| 5,569,234 A | 10/1996 | Buell et al. |
| 5,643,588 A | 1/1997 | Roe et al. |
| 5,635,191 A | 3/1997 | Roe et al. |
| 5,607,760 A | 4/1997 | Roe |
| 5,625,222 A | 4/1997 | Yoneda et al. |
| 5,637,665 A | 6/1997 | Sustic et al. |
| 5,591,152 A | 7/1997 | Buell et al. |
| 5,681,913 A | 10/1997 | Sustic et al. |
| 5,609,587 A | 11/1997 | Roe |
| 5,685,758 A | 11/1997 | Paul et al. |
| 5,714,554 A | 2/1998 | Sustic et al. |
| 5,723,546 A | 3/1998 | Sustic |
| 5,804,519 A | 9/1998 | Riswick et al. |
| 5,865,823 A | 2/1999 | Curro |
| 5,897,545 A | 4/1999 | Kline et al. |
| 5,957,908 A | 4/1999 | Kline et al. |
| 5,998,547 A | 12/1999 | Hohner |
| 6,004,306 A | 12/1999 | Roe et al. |
| 6,107,537 A | 8/2000 | Elder et al. |
| 6,120,487 A | 9/2000 | Buell et al. |
| 6,120,489 A | 9/2000 | Johnson et al. |
| 6,143,818 A | 11/2000 | Wang et al. |
| 6,218,457 B1 * | 4/2001 | Fralich | C09J 123/20 524/270 |
| 6,281,288 B1 | 8/2001 | Bickert et al. |
| 6,432,098 B1 | 8/2002 | Kline et al. |
| 6,486,246 B1 | 11/2002 | Vion |
| 6,489,400 B2 | 12/2002 | Khandpur et al. |
| 6,582,762 B2 | 6/2003 | Faissat et al. |
| 6,657,009 B2 | 12/2003 | Zhou |
| 6,677,396 B2 | 1/2004 | Tsui et al. |
| 6,747,114 B2 | 6/2004 | Karandinos et al. |
| 6,767,424 B1 | 7/2004 | Butterbach et al. |
| 6,773,818 B2 | 8/2004 | Cretekos et al. |
| 6,887,941 B2 | 5/2005 | Zhou |
| 6,992,131 B2 | 1/2006 | Faissat et al. |
| 7,067,585 B2 | 6/2006 | Wang et al. |
| 7,163,741 B2 | 1/2007 | Khandpur et al. |
| 7,199,180 B1 | 4/2007 | Simmons et al. |
| 7,262,251 B2 | 8/2007 | Kanderski et al. |
| 7,270,889 B2 | 9/2007 | Campbell et al. |
| 7,348,376 B2 | 3/2008 | Gelles |
| 7,626,073 B2 | 1/2009 | Catalan |
| 7,517,579 B2 | 4/2009 | Campbell et al. |
| 7,521,507 B2 | 4/2009 | Lewtas et al. |
| 7,524,910 B2 | 4/2009 | Jiang et al. |
| 7,833,611 B2 | 11/2010 | Phan et al. |
| 7,927,703 B2 | 4/2011 | Xia et al. |
| 8,017,827 B2 | 9/2011 | Hundorf et al. |
| 8,084,527 B2 | 12/2011 | Paschkowski et al. |
| 8,193,289 B2 | 6/2012 | Abhari et al. |
| 8,226,625 B2 | 7/2012 | Turner et al. |
| 8,226,626 B2 | 7/2012 | Turner et al. |
| 8,231,595 B2 | 7/2012 | Turner et al. |
| 8,388,594 B2 | 5/2013 | Turner et al. |
| 8,496,637 B2 | 7/2013 | Hundorf et al. |
| 8,865,824 B2 | 10/2014 | Bunnelle |
| 9,139,755 B2 | 9/2015 | Bunnelle |
| 9,187,679 B2 | 11/2015 | Bunnelle |
| 9,241,843 B2 | 1/2016 | Bunnelle |
| 9,670,388 B2 | 6/2017 | Bunnelle |
| 2004/0038058 A1 | 2/2004 | Zhou |
| 2004/0204529 A1 * | 10/2004 | Gipson | C08L 21/00 524/474 |
| 2007/0042193 A1 | 2/2007 | Wang |
| 2007/0055211 A1 | 3/2007 | Shunketsu et al. |
| 2007/0117894 A1 | 5/2007 | Bach et al. |
| 2007/0117907 A1 | 5/2007 | Bach et al. |
| 2007/0142801 A1 | 6/2007 | Zhou et al. |
| 2007/0187032 A1 | 8/2007 | Wang |
| 2008/0312617 A1 | 12/2008 | Hundorf et al. |
| 2008/0312618 A1 | 12/2008 | Hundorf et al. |
| 2008/0319116 A1 | 12/2008 | Fredrickson et al. |
| 2010/0160497 A1 | 6/2010 | Karjala et al. |
| 2011/0021102 A1 | 1/2011 | Inoue et al. |
| 2011/0052929 A1 | 3/2011 | Nairn et al. |
| 2011/0082256 A1 | 4/2011 | Martinez et al. |
| 2011/0104508 A1 | 5/2011 | Wang et al. |
| 2011/0167074 A1 | 7/2011 | Heinze et al. |
| 2012/0149827 A1 | 6/2012 | Hu et al. |
| 2012/0171466 A1 | 7/2012 | Urbach et al. |
| 2012/0178333 A1 | 7/2012 | Fowler et al. |
| 2012/0328805 A1 | 12/2012 | Davis |
| 2012/0329353 A1 | 12/2012 | Davis et al. |
| 2013/0158176 A1 * | 6/2013 | Hu | C09J 5/06 524/274 |
| 2014/0079919 A1 * | 3/2014 | Bunnelle | C09J 123/18 428/195.1 |
| 2015/0173958 A1 * | 6/2015 | Bunnelle | A61F 13/15203 604/366 |
| 2015/0174281 A1 | 6/2015 | Bunnelle |
| 2015/0174286 A1 * | 6/2015 | Bunnelle | A61F 13/15203 604/365 |
| 2016/0068716 A1 | 3/2016 | Bunnelle |
| 2017/0204307 A1 | 7/2017 | Bunnelle |

FOREIGN PATENT DOCUMENTS

| | | |
|---|---|---|
| CN | 1372586 | 10/2002 |
| WO | WO1998049249 | 11/1998 |
| WO | WO1998049249 A1 | 11/1998 |
| WO | WO2002053669 | 7/2002 |
| WO | WO2007026334 | 3/2007 |
| WO | WO 2012/027450 | 3/2012 |
| WO | WO2013019507 | 2/2013 |
| WO | WO2014047317 | 3/2014 |

* cited by examiner

HOT MELT ADHESIVE

This application claims priority to U.S. Provisional Patent Application No. 61/918,434, filed Dec. 19, 2013, entitled "Hot Melt Adhesive", the contents of which are hereby incorporated by reference in their entirety.

Disclosed is a general purpose hot melt adhesive material that can be applied to substrates such as cellulosic materials, film, fiber or nonwovens in the construction of articles. The adhesive composition is manufactured to obtain melt viscosity, cohesion and adhesion sufficient to assemble an article and obtain a mechanically stable product. The adhesive typically comprises a blend of polymer materials combined at proportions that obtain the desired and useful construction properties useful in the manufacture of articles. One embodiment is the hot melt adhesive. A second embodiment is an article manufactured using the construction properties and aspects of the hot melt adhesive.

Common hot melt adhesives are made by combining polymer and additive in a substantially uniform thermoplastic blend. Improved materials are needed for use in improved application equipment and in current and updated article constructions. A substantial need exists in providing new formulation combinations of materials and blending techniques that obtain improved adhesives.

The adhesive composition comprises a first amorphous α-olefin copolymer and a second polymer. The amorphous polymer comprises an amorphous or random polymer comprising butene and one or more an alpha olefin monomer such as ethylene, propene, pentene, octene etc. The second polymer comprises an amorphous material that can act as a diluent, viscosity modifier, extender or plasticizer.

As used herein "homopolymer" means a polymer resulting from the polymerization of a single monomer, i.e., a polymer consisting essentially of a single type of repeating unit.

As used herein, the term "copolymer(s)" refers to polymer(s) formed by the polymerization of at least two different monomers. For example, the term "copolymer" includes the copolymerization reaction product of a monomer such as propene or butene, preferably 1-butene and an α-olefin, such as for example, ethylene, 1-hexene or 1-octene.

As used herein, the term "propene copolymer" or "propylene copolymer" means a copolymer of greater than 40 or 50 wt. % or more propene and at least one monomer selected from the group including ethylene and a $C_4$ to $C_{20}$ α-olefin.

As used herein, the term "butene copolymer" means a polymer of n-butene (1-butene) or 2-butene and at least one monomer selected from the group of $C_{2-3}$ and $C_{5-20}$ alpha olefins. Butene copolymers typically comprise a minimum amount at least about 40 or about 50 wt. % or more of a butene monomer such as 1-butene.

The term "amorphous" means the substantial absence of crystallinity, (i.e.) less than 5% and less than 1%. The term "heterophase" polymer means a polymer having an amorphous character and at least some substantial crystalline content (at least 5 wt. %, 10 wt. %, 20 wt. %, 40 wt. % or 50 wt. % crystalline content) that can provide cohesive strength in the cooled adhesive mass. The crystalline content can be in the form of stereoregular blocks or sequences.

The term "sequence or block" means a polymer portion of repeating monomer that is similar in composition, crystallinity or other aspect.

As used herein, the term "open time" means the amount of time elapsed between application of a molten hot melt adhesive composition to a first substrate, and the time when useful tackiness or wetting out of the adhesive on a substrate effectively ceases due to solidification of the adhesive composition. Open time is also referred to as "working time."

As used herein, the term "substrate" means any item having at least a partially or fully solidified fiber, film or planar surface with which contact with a hot melt adhesive composition is intended. In some cases the same area, circle, bead, line, filament or dot of hot melt adhesive composition is contacted with two or more substrates for the purpose of creating an adhesive bond there between. In some such cases the substrates are part of the same item: for example, folded film or folded non-woven, two sides of a cardboard sheet folded over, wherein the two sides are adhesively bonded together. In other such cases the substrates are part of different items: for example, a plastic film that is adhesively bonded to a second film, a non-woven or cardboard sheet. The substrates can be impermeable, permeable, porous or nonporous.

As used herein, the term "substantially" means generally the same or uniform but allowing for or having minor fluctuations from a defined property, definition, etc. For example, small measurable or immeasurable fluctuations in a measured property described herein, such as viscosity, melting point, etc. may result from human error or methodology precision. Other fluctuations are caused by inherent variations in the manufacturing process, thermal history of a formulation, and the like. The adhesive compositions of the, nonetheless, would be said to be substantially having the property as reported.

As used herein, the term "major proportion" means that a material or monomer is used at greater than 50 wt. %. As used herein, the term "primary component" means that a material or monomer is the more common substance or has the higher concentration in the mixture or polymer compared to others but may not be as much as 50 wt. %.

The transitional phrase "consisting essentially of" limits the scope of a claim to the specified materials but includes those that do not materially affect the basic and novel characteristics of the claimed materials. These characteristics include open time, cohesive strength (tensile strength), peel strength and viscosity. Meaningful amounts of a third polymer or amounts of a tackifier materially affect the basic and novel characteristics of the claimed materials.

The adhesive material comprises a first polymer comprising a polyolefin copolymer comprising a substantially amorphous or randomly polymerized polymer material comprising 1-butene and a second amorphous polymer comprising a compatible amorphous liquid butene polymer such as a polyisobutylene polymer or similar material. The polyisobutylene polymer comprising a substantial proportion (greater than 50 mole % and often greater than 90 mole %) of a isobutylene monomer.

The first amorphous polymer comprises typically butene (e.g.) 1-butene and can be a copolymer or terpolymer that can contain ethylene, propene or a second $C_{4-40}$ olefin polymer. These substantially amorphous low crystallinity polymers have less than 10% and preferably less than 5% crystalline character.

The amorphous polymer is a butene-based copolymer (the minimum amount is at least about 30 or 40 or 50 or 60 wt. % of 1-butene), which may also be referred to as a random butene-α-olefin copolymer. The butene copolymer includes one or more units, i.e., monomer units, derived from propene, one or more comonomer units derived from ethylene or α-olefins including from 4 to about 20 carbon atoms.

The first copolymer comprises about 30 mole %—about 75 mole %, preferably about 40 mole % to about 70 mole %, about 50 mole %—about 65 mole %, of units derived from butene. In addition to butene-derived units, the present copolymer contains from about 70 mole %—about 30 mole % to about 60 mole %—about 40 mole %, of units derived from preferably ethylene, propene or at least one $C_{5\ to\ 10}$ alpha-olefin monomer.

In one or more embodiments, the α-olefin comonomer units can also be derived from other monomers such as ethylene, 1-butene, 1-hexane, 4-methyl-1-pentene and/or 1-octene. Exemplary alpha-olefins are selected from the group consisting of ethylene, butene-1, pentene-1,2-methylpentene-1,3methylbutene-1, hexene-1,3-methylpentene-1, 4-methylpentene-1,3,3-dimethylbutene-1, heptene-1, hexene-1, methylhexene-1, dimethylpentene-1, trimethylbutene-1, ethylpentene-1, octene-1, methylpentene-1, dimethylhexene-1, trimethylpentene-1, ethylhexene-1, methylethylpentene-1, diethylbutene-1, propylpentane-1, decene-1, methylnonene-1, nonene-1, dimethyloctene-1, trimethylheptene-1, ethyloctene-1, methylethylbutene-1, diethylhexene-1, dodecene-1, and hexadodecene-1.

In one or more embodiments, amorphous copolymer comprises about 30 mole %—about 75 mole %, preferably about 40 mole % to about 00 mole % of units derived from butene and from about 70 mole %—about 30 mole % to about 60 mole %—about 40 mole %, about 50 mole %—about 65 mole %, of units derived from at least one alpha-olefin monomer selected from ethylene, propene, 1-hexene or 1-octene. Small amounts of α-olefin monomer(s) can be used in the range of about 0.1 to 20 mole %. The amorphous polymer has a weight average molecular weight (Mw) of about 1,000 to about 25,000 or less, preferably about 2,000 to 20,000.

In one or more embodiments, first copolymer comprises about 30 mole %—about 70 mole %, preferably about 40 mole % to about 60 mole % of units derived from butene and from about 70 mole %—about 30 mole % to about 60 mole %—about 40 mole %, of units derived from propene, while small amounts of α-olefin monomer(s) can be used in the range of about 0.1 to 20 mole %.

The amorphous polymer has a weight average molecular weight (Mw) of about 1,000 to about 50,000 or less, preferably about 5,000 to 45,000.

The amorphous copolymer has a viscosity of less than 10,000 mPa·s (1 centipoise [cps]=1 mPa·s), for example about 2000 to 8000 mPa·s, when measured by ASTM D3236 at 190° C. Melt Viscosity was determined according to ASTM D-3236, which is also referred to herein as "viscosity" and/or "Brookfield viscosity".

Some examples of amorphous polyolefin include the Rextac polymers made by Huntsman including Rextac E-62, E-65. See, for example Sustic, U.S. Pat. No. 5,723,546 for a description of the polymers and which is expressly incorporated herein. Other useful amorphous polymers are sold as Vestoplast® and Eastoflex® materials.

The adhesive material comprises a second polymer that is compatible with the 1-butene component in the first copolymer. Such compatibility arises from a liquid amorphous material comprising at least one butene monomer (1-butene, cis and trans-2-butene, and isobutylene) isomer. Unlike conventional plasticizing oils such as white oils having a conventional hydrocarbon character, useful materials are sufficiently compatible and as a result improve add-on processability characteristics, reduce viscosity, maintain adhesive bond while improving cohesive properties. The term "compatible or compatibility" of a blend of polymers, as the term is used in this disclosure, means that (1) the materials blend into a uniform hot melt and (2) the cohesive strength of a mixture (70/30 to 50/50) by weight of the amorphous 1-butene polymer and the second amorphous polymer is maintained for construction purposes. Preferred materials comprise a compatible extender, diluent, and viscosity modifier such as a polyisobutylene polymer. The polymer can comprise major proportion of isobutylene units or can be represented as:

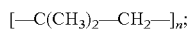

$[-C(CH_3)_2-CH_2-]_n;$ wherein n=15 to 75. Preferred materials such as a Polyisobutylene are viscous liquids with molecular weight of about 200-20,000, about 200-5,000 or about 500-3,000. The preferred liquid materials have a Saybolt Universal seconds (SUS) viscosity at 100° C. of about 100 to 20,000. The characteristic features of polyisobutylene are low gas permeability and high resistance to the action of acids, alkalis, and solutions of salts, as well as high dielectric indexes. They degrade gradually under the action of sunlight and ultraviolet rays (the addition of carbon black slows this process). In industry, polyisobutylene is produced by ionic ($AlCl_3$ catalyzed) polymerization of the monomer at temperatures from −80° to −100° C.; they are processed using the ordinary equipment of the rubber industry. Polyisobutylene combines easily with natural or synthetic rubbers, polyethylene, polyvinyl chloride, and phenol-formaldehyde resins.

In some embodiments, the plasticizers include polypropylene, polybutene, hydrogenated polyisoprene, hydrogenated polybutadiene, polypiperylene, copolymers of piperylene and isoprene, and the like, having average molecular weights between about 350 and about 10,000. In other embodiments, the plasticizers include glyceryl esters of the usual fatty acids.

As noted above, embodiments of preferred compositions are made substantially free of an effective amount of a conventional tackifier material that can add any aspect of open time, substrate wetting or tack to the adhesive material. Avoiding the use of a tackifier reduces costs and frees formulators from the use of materials in short supply. Further, tackifier can impart undesirable odor in disposable articles and can also act as carriers of low molecular weight plasticizers (like process oils that are used in SBC based adhesives) that can weaken the polyethylene back sheet materials used in baby diapers. Back sheet integrity is becoming more important due to the downsizing of the polyethylene film thickness used in these articles. By the term "conventional tackifier resins", those resins commonly available in the adhesive art and industry that are used in typical hot melt adhesives. Examples of conventional tackifying resins included in this range include an aliphatic hydrocarbon resins, aromatic modified aliphatic hydrocarbon resins, hydrogenated poly-cyclopentadiene resins, poly-cyclopentadiene resins, gum rosins, gum rosin esters, wood rosins, wood rosin esters, tall oil rosins, tall oil rosin esters, poly-terpene, aromatic modified poly-terpene, terpene-phenolic, aromatic modified hydrogenated poly-cyclopentadiene resins, hydrogenated aliphatic resins, hydrogenated aliphatic aromatic resins, hydrogenated terpene and modified terpene and hydrogenated rosin esters. Often in conventional formulations such resins are used in amounts that range from about 5 to about 65 wt. %. often about 20 to 30 wt. %.

In further embodiments, the compositions disclosed herein optionally can comprise an antioxidant or a stabilizer. Any antioxidant known to a person of ordinary skill in the art may be used in the adhesion composition disclosed herein. Non-limiting examples of suitable antioxidants include amine-based antioxidants such as alkyl diphenyl amines, phenyl-naphthylamine, alkyl or aralkyl substituted phenyl-naphthylamine, alkylated p-phenylene diamines, tetramethyl-diaminodiphenylamine and the like; and hindered phenol compounds such as 2,6-di-t-butyl-4-methyl-phenol; 1,3,5-trimethyl-2,4,6-tris(3',5'-di-t-butyl-4'-hydroxybenzyl)benzene; tetra kis [(methylene(3,5-di-t-butyl-4-hydroxyhydrocinnamate)]methane (e.g., IRGANOX™1 010, from Ciba Geigy, N.Y.); octadecyl-3,5-di-t-butyl-4-hydroxycinnamate (e.g., IRGANOX™ 1076, commercially available from Ciba Geigy) and combinations thereof. Where used, the amount of the antioxidant in the composition can be from about greater than 0 to about 1 wt. %, from about 0.05 to about 0.75 wt. %, or from about 0.1 to about 0.5 wt. % of the total weight of the composition.

In further embodiments, the compositions disclosed herein optionally can comprise an UV stabilizer that may prevent or reduce the degradation of the composition by radiation. Any UV stabilizer known to a person of ordinary skill in the art may be used in the adhesion composition disclosed herein. Non-limiting examples of suitable UV stabilizers include benzophenones, benzotriazoles, aryl esters, oxanilides, acrylic esters, formamidine carbon black, hindered amines, nickel quenchers, hindered amines, phenolic antioxidants, metallic salts, zinc compounds and combinations thereof. Where used, the amount of the W stabilizer in the composition can be from about greater than 0 to about 1 wt. %, from about 0.05 to about 0.75 wt. %, or from about 0.1 to about 0.5 wt. % of the total weight of the composition.

In further embodiments, the compositions disclosed herein optionally can comprise a brightener, colorant or pigment. Any colorant or pigment known to a person of ordinary skill in the art may be used in the adhesion composition disclosed herein. Non-limiting examples of suitable brighteners, colorants or pigments include fluorescent materials and pigments such as triazine-stilbene, coumarin, imidazole, diazole, titanium dioxide and carbon black, phthalocyanine pigments, and other organic pigments such as IRGAZINB, CROMOPHTALB, MONASTRALB, CINQUASIAB, IRGALITEB, ORASOLB, all of which are available from Ciba Specialty Chemicals, Tarrytown, N.Y. Where used, the amount of the brightener, colorant or pigment in the composition can be from about greater than 0 to about 10 wt %, from about 0.01 to about 5 wt %, or from about 0.1 to about 2 wt % of the total weight of the composition.

The compositions disclosed herein may also optionally comprise a fragrance such as a perfume or other odorant. Such fragrances may be retained by a liner or contained in release agents such as microcapsules that may, for example, release fragrance upon removal of a release liner from or compression on the composition.

In further embodiments, the compositions disclosed herein optionally can comprise filler. Any filler known to a person of ordinary skill in the art may be used in the adhesion composition disclosed herein. Non-limiting examples of suitable fillers include sand, talc, dolomite, calcium carbonate, clay, silica, mica, wollastonite, feldspar, aluminum silicate, alumina, hydrated alumina, glass bead, glass microsphere, ceramic microsphere, thermoplastic microsphere, barite, wood flour, and combinations thereof. Where used, the amount of the filler in the composition can be from about greater than 0 to about 60 wt. %, from about 1 to about 50 wt. %, or from about 5 to about 40 wt. %

TABLE 1

Exemplary Tackifier free Adhesive Compositions

| Component | Embodiment | Wt. % | Wt. % | Wt. % |
|---|---|---|---|---|
| Amorphous polymer | REXTAC E63 or E65 or blends (Sustic technology) | 90-10 | 30-85 | 75-40 |
| Second Amorphous Polymer | Polyisobutylene | 0-50 | 5-45 | 5-40 |
| Additive | Extender/diluent | 0-30 | 0.1-20 | 0.1-10 |
| Additive | Brightener | 0.001-0.3 | 0.001-0.1 | 0.001-0.05 |
| Additive | Antioxidant/stabilizer | 0-20 | 1-20 | 1-15 |

The hot melt adhesive compositions have melt rheology and thermal stability suitable for use with conventional hot melt adhesive application equipment. The blended components of the hot melt adhesive compositions have low melt viscosity at the application temperature, thereby facilitating flow of the compositions through a coating apparatus, e.g., coating die or nozzle, without resorting to the inclusion of solvents or extender oil into the composition. Melt viscosities of the hot melt adhesive compositions are between 1500 cP and 3500 cP or about 2000 cP to 3000 cP in mille Pascal-seconds or centipoise (cP) using a Brookfield thermosel RVT viscometer using a rotor number 27 at 176.66° C. (50 rpm, 350° F.). The hot melt adhesive compositions have a softening point (ASTM D 3461-97 Standard Test Method for Mettler Softening Point Method) of about 80° C. to 140° C., in some embodiments about 115° C. to 130° C. Typical but non-limiting industrial applications of the hot melt adhesive compositions include sanitary disposable consumer articles, made of non-woven materials, films, microporous films etc. for example, diapers, feminine care pads, napkins, hospital surgical drapes and pads etc. that benefit from both the low temperature flexibility, heat resistance and the efficiency of end use in automated means of applying the hot melt adhesive compositions to various substrates.

Articles include items having any two or more substrates adhesively bonded by a hot melt adhesive composition. The substrates that are adhesively bonded in such articles are formed from materials such as cardboard, paper, thermoplastics such as polyesters such as polyethylene terephthalate, polyamides such as nylons, or polypropylene, thermoset polymers, and combinations, blends, or layered composites thereof and include, in some embodiments, coatings of wax, acrylate polymers, or other materials; colorants, preservatives, stabilizers, processing lubricants, and the like as well as combinations of any of these materials. The substrates include solid, nonporous items and sheets as well as porous items and sheets, such as nonwoven fabrics, paper, cotton batting, stretchable and breathable polypropylene and polyethylene and copolymers and the like.

Another aspect are methods of manufacture employing the hot melt adhesive compositions. The method involves application of the molten compositions to a substrate, followed by contact of the adhesive composition with a second substrate within 0.1 second to 5 seconds after application of the adhesive composition to the first substrate, wherein the contacting results in an adhesive bond between the substrates.

Yet another aspect is an article of manufacture including the hot melt adhesive compositions, wherein the article includes at least two substrates adhesively bonded by an amount of a hot melt adhesive composition. Typical articles of manufacture include sanitary disposable consumer articles, for example, diapers, feminine care pads, napkins, and the like articles such as those formed from a combination of low energy and higher energy materials, for example a pulp or cardboard having a polyethylene wrap and/or a polypropylene label, or a non-woven having a protective plastic top. In general, articles that are advantageously bonded using the hot melt adhesive compositions benefit from both the low temperature flexibility, heat resistance and the efficiency of end use in automated means of applying the adhesive compositions to substrates.

Hot melt adhesive compositions were formulated by melt blending as described below, wherein specific components and amounts of the components are shown below. In the articles manufactured using the adhesives, the articles can be manufactured by forming an adhesive bond between a polymer film and a fiber or fiber mass. The article can also comprise an adhesive bond formed between a polymer film and a nonwoven fabric. Additionally the article can be manufactured by forming an adhesive bond between a multi layer structure comprising the exterior layer of a polymer film and interior components comprising a fiber map or a nonwoven fabric.

The adhesive materials can be used as a construction adhesive in assembly of commonly available consumer disposal articles. Such articles include infant diapers, adult diapers, bed pads, sanitary products, and other absorbent articles. Combining at least a polymer film with other films and fibrous materials typically makes these articles. Fibrous materials can include fabrics such as woven or nonwoven fabrics, fibers in the form of fiber mats, fiber collections, fiber balls, etc.

Such absorbent articles typically comprise an absorbent held within the article. The absorbent is usually covered using a nonwoven inner liner. Such liners comprise a highly permeable material such as a spun bonded nonwoven structure that passes fluids or moisture from the interior of the article into the absorbent layer. The absorbent layer or structure formed within the absorbent article typically comprises a fiber mass pad or cellulosic or wood pulp for the purpose of substantially absorbing liquid or fluid materials released into the absorbent article. The fiber or fluff can comprise a cellulosic fiber, a synthetic fiber or mixtures thereof such as blends of wood fiber, cellulosic fiber, polyethylene fiber, polypropene fiber or other fiber materials often including a super absorbent material. Super or highly absorbent materials are used to increase the absorptive capacity of the absorbent article. Such materials are organic materials including modified natural gums and resins but often include synthetic polymer materials such as hydrogels. Carboxy-methyl Cellulose, alkaline metal salts of acrylic polymers, polyacrylamides, polyvinyl alcohol, polyethylene anhydride polymers and copolymers, polyvinyl ether polymers and copolymers, hydroxyalkyl cellulose polymers and copolymers, polyvinyl sulfonic acid polymers and copolymers, polyacrylic polymers, polyvinyl-pyrrolidone polymers and copolymers can be used in the absorbent function.

Nonwoven fabric layers used in such disposal articles typically are generally planar structures comprising a bonded assembly of natural or synthetic fiber.

Such nonwoven materials are often made using a variety of techniques, including spun bonding, melt bonding, etc. Such nonwoven materials are often manufactured by randomly placing fibers or rovings in a substantially random pattern and are then thermally bonded using inherent bonding characteristics of the fibers or by bonding the fibers using resin materials applied to the fibers. Various polymers can be used to make nonwoven materials including poly olefins, polyesters, ethylene vinyl acetate polymers, ethylene acrylic acid polymers and others.

The exterior of the article often comprises a polymer film that is liquid impervious. In certain aspects exterior polymer films can be further modified using additional exterior layers to obtain a more cloth like or nonwoven character to the exterior polymer film. The exterior film typically comprises a single layer of a polymer film but can be a multi-layer film structure. Typical polymer sheet materials comprise high tensile strength polymers including polyesters, poly olefins or other thermoplastic sheet materials that can be formed into film layers. The polyolefin or polyester polymer materials are often formed into sheets and are treated to improve strength, flexibility and puncture resistance. Techniques including biaxial orientation, heat treatment or surface treatment can improve the film characteristics of the polymer films. Such polymer films often have a thickness that ranges from about ten to about one hundred microns.

One embodiment of an absorbent article that we have mentioned comprises the impervious and breathable polymer film and fabric, an absorbent layer pad or mat and a nonwoven interior layer. This three component structure is assembled using the adhesive that is applied using manufacturing techniques that adheres the nonwoven interior layer to the polymer film while holding the absorbent layer there between.

The adhesive compositions can be applied under melt conditions to a substrate as a hot melt adhesive or may be coated, applied or sprayed onto the polymer film nonwoven or absorbent pad. Adhesives are typically applied using slot coat, spray-on or atomizing character in a bead, dot pattern, spiral pattern or other conventional pattern using such Nordson application techniques. In a preferred embodiment, the composition of the adhesive composition is applied to a substrate using a slot coat (using Nordson true coat or Speed coat slot) at increased machine speed.

The material is typically applied in an amount of about 0.1 to about 20 or about 0.2 to about 10 or about 0.3 to about 15 grams per square meter (g-m$^{-2}$) of resulting bonded material. The adhesive material can be used at an add-on rate of 0.5 to 2 g-m$^{-2}$, 0.6 to 1.7 g-m$^{-2}$ or 0.7 to 1.5 g-m$^{-2}$, for sanitary products or disposable diaper articles. Similar low add-on rates can be accomplished for napkin construction, elastic attachment and other disposable goods. Particularly preferred applications for the materials disclosed are include baby diaper construction, diaper chassis construction, diaper core stabilization, diaper outer cover lamination, feminine napkin construction and core stabilization, feminine napkin adhesive strip, etc.

EXPERIMENTAL

A number of hot melt adhesive compositions were prepared by blending first amorphous copolymer, second compatible copolymer and antioxidant under mixing conditions at elevated temperatures to form a fully homogenized melt. Mixing temperatures varied from about 135 to about 200° C. preferably about 150 to about 175° C. as needed to obtain uniformity. A traditional heated stirred blade (WiseStir®) mixer was used to ensure full homogenization in a heated container into a final adhesive composition.

Examples 1-3

Hot melt adhesive compositions were formulated by melt blending, as described below, wherein specific components and amounts of the components are shown in the following table 2.

TABLE 2

Experimental Preparations

| Component | Ex. 1 (wt. %) | Ex. 2 (wt. %) | Ex. 3 (wt. %) |
| --- | --- | --- | --- |
| Rextac E-65 (1-butene copolymer) | 44.5 | 54.5 | |
| Rextac E-63 (1-butene copolymer) | 30 | 20 | |
| Rextac 2830 (1-butene copolymer) | | | 70 |
| Indapol H-1900 Polyisobutylene (MW2500) | 24.99 | 24.99 | 29.49 |
| Irganox 1010 (Stabilizer) | 0.5 | 0.5 | 0.5 |
| Benotex OB (Optical brightener) | 0.01 | 0.01 | 0.01 |
| Brookfield DV-II + pro Viscosity (cP) Rotation 10 rpm Spindle # SC4-27 | | | |
| 250° F. | 31000 | 23825 | 18200 |
| 275° F. | 13650 | 13175 | 10250 |
| 300° F. | 6265 | 6875 | 6050 |
| 325° F. | 4090 | 4460 | 3850 |
| 350° F. | 3245 | 3060 | 2595 |
| Mettler Softening Point (° C.) | 116 | 115 | 91 |
| Density (g-cm$^{-3}$) | 0.87 | 0.87 | 0.87 |

Comparative Example 1

Hot melt adhesive compositions is formulated by melt blending, as described below, wherein specific components and amounts of the components are shown in the following table 3.

TABLE 3

Experimental Preparations

| Component | CEx. 1 (wt. %) | CEx. 2 (wt. %) |
| --- | --- | --- |
| APAO | | 75 |
| Rextac E-63 (1-butene copolymer) | 75 | |
| Polyisobutylene | | 25 |
| White Oil | 25 | |
| Irganox 1010 (Stabilizer) | 0 | 0 |
| Benotex OB (Optical brightener) | 0 | 0 |

Comparative examples 1 and 2 forms a non-uniform composition that has insufficient cohesive/adhesive strength to be usefully measured.

TABLE 4

Test Results

| Run | Add-on method - Nordsen ® Hot Melt applic. | Add-on (g-m$^{-2}$) Over 120 mm width | Temp (° F./° C.) | Gap | Air Press. (psi/ Pascal) | Web Speed (inch-sec$^{-1}$/ m-sec$^{-1}$) | Ex. | Ex. | Ex. | Peak Peel (g-in$^{-1}$) | Average Peel (g-in$^{-1}$) | Peel force (N-cm$^{-1}$) |
| --- | --- | --- | --- | --- | --- | --- | --- | --- | --- | --- | --- | --- |
| 1 | Slot/true coat die | 0.75 | 320/160 | | | 2000/50.8 | Ex. 2 | | | 190 | 93 | 0.37 |
| 2 | Slot/true coat die | 1 | 310/154.4 | | | 2000/50.8 | Ex. 2 | | | 202 | 110 | 0.43 |
| 3 | Slot/true coat die | 1 | 320/160 | | | 2000/50.8 | Ex. 2 | | | 217 | 134 | 0.53 |
| 4 | Slot/true coat die | 1 | 330/165.6 | | | 2000/50.8 | Ex. 2 | | | 212 | 131 | 0.52 |
| 5 | Slot/true coat die | 1 | 315/157.2 | | | 2000/50.8 | Ex. 2 | | | 205 | 110 | 0.43 |
| 6 | Slot/true coat die | 0.5 | 320/160 | | | 2000/50.8 | Ex. 2 | | | 111 | 58 | 0.23 |
| 7 | Slot/true coat die | 0.75 | 320/160 | | | 2000/50.8 | Ex. 2 | | | 161 | 95 | 0.37 |
| 8 | Slot/true coat die | 0.5 | 320/160 | | | 2000/50.8 | | Ex. 1 | | 126 | 70 | 0.28 |
| 9 | Slot/true coat die | 0.75 | 320/160 | | | 2000/50.8 | | Ex. 1 | | 181 | 100 | 0.39 |
| 10 | Slot/true coat die | 0.5 | 320/160 | | | 2000/50.8 | | | Ex. 3 | 117 | 62 | 0.24 |
| 11 | Slot/true coat die | 0.75 | 320/160 | | | 2000/50.8 | | | Ex. 3 | 152 | 93 | 0.37 |
| 12 | Slot/true coat die | 1 | 320/160 | | | 2000/50.8 | | | Ex. 3 | 192 | 123 | 0.48 |
| 13 | Signature | 1 | 360/182.2 | 20 mm | 40/0.276 | 2000/50.8 | Ex. 2 | | | 154 | 92 | 0.36 |
| 14 | Signature | 1 | 360/182.2 | 20 mm | 45/0.310 | 2000/50.8 | Ex. 2 | | | 164 | 96 | 0.38 |
| 15 | Signature | 1 | 360/182.2 | 25 mm | 45/0.310 | 2000/50.8 | Ex. 2 | | | 189 | 102 | 0.4 |
| 16 | Signature | 1.25 | 360/182.2 | 25 mm | 45/0.310 | 2000/50.8 | Ex. 2 | | | 201 | 123 | 0.48 |
| 17 | Signature | 1.25 | 360/182.2 | 25 mm | 45/0.310 | 2000/50.8 | | | Ex. 3 | 187 | 116 | 0.46 |
| 18 | Signature | 1 | 360/182.2 | 25 mm | 45/0.310 | 2000/50.8 | | | Ex. 3 | 158 | 88 | 0.35 |
| 19 | Signature | 1 | 360/182.2 | 25 mm | 45/0.310 | 2000/50.8 | | Ex. 1 | | 197 | 122 | 0.48 |
| 20 | Signature | 1.25 | 360/182.2 | 25 mm | 45/0.310 | 2000/50.8 | | Ex. 1 | | 232 | 138 | 0.54 |

All tests show adhesion and good bonding. The data from runs 2, 3, 4, 5, 9, 12, 15, 16, 17, 19 and 20 show values that all exceeded requirements for a successful construction manufacture.

These data indicates that the materials will provide excellent construction bonding in disposable absorbent articles. Note viscosity relates to the resistance to flow of the material under certain conditions. This distinctive property determines the flowability, degree of wetting, and penetration of the substrate by the molten polymer. It provides an indication of its processability and utility as a hot melt adhesive material.

Melt viscosity is generally directly related to a polymer molecular weight and is reported in millipascal-second (mP·s) or centipoise (cP) using a Brookfield DV-II+Pro (Rotation 10 rpm—Spindle # SC4-27) at the stated temperature Mettler softening point in degrees Centigrade or degrees Fahrenheit is typically measured using ASTM D3104. The amorphous nature of the poly olefin materials results in a melting point, which is not sharp or definite. Rather as the temperature increases, amorphous polymers gradually change from a solid to a soft and then to a liquid material. No clearly defined glass transition or melting temperature is often noted. This temperature testament that generally measures the precise temperature at which a disc of polymer sample, heated at a rate of 2° C. per minute or 10° F. per minute becomes soft enough to allow the test object, a steel ball (grams) drops through the sample. The softening point of a polymer reported in degrees Centigrade or degrees Fahrenheit is important because it typically indicates the polymer's heat resistance, useful application temperatures and solidification points.

Peel test values were obtained by forming a laminate from a SMS non-woven (11.6 g-m$^{-2}$) micro-porous polyethylene film (0.5 mil/0.127 micron) using lamination conditions as shown in Table 4. The laminate is cut into 1 inch/25.4 mm wide strips in the cross machine direction. Peel force was measured by separating the laminate at room temperature using a TMax pull tester at a rate of 20 in-sec$^{-1}$/50.8 cm-sec$^{-1}$ with the peek force averaged over a 15 period.

The claims may suitably comprise, consist of, or consist essentially of, or be substantially free of any of the disclosed or recited elements. The invention illustratively disclosed herein can also be suitably practiced in the absence of any element which is not specifically disclosed herein. The various embodiments described above are provided by way of illustration only and should not be construed to limit the claims attached hereto. Various modifications and changes may be made without following the example embodiments and applications illustrated and described herein, and without departing from the true spirit and scope of the following claims.

I claim:

1. A hot melt adhesive composition comprising:
    (i) from about 50 wt. % to about 90 wt. % of an amorphous polyolefin copolymer comprising more than 40 mole % 1-butene, the amorphous polyolefin copolymer having a viscosity of between 2000 and 8000 cps at a temperature of about 190° C.; and
    (ii) from about 10 wt. % to about 50 wt. % of a second amorphous polymer comprising at least one butene monomer, the second amorphous polymer having a molecular weight ($MW_n$) of at least 1000, wherein the second amorphous polymer is compatible with the amorphous polyolefin copolymer.

2. The hot melt adhesive composition of claim 1, wherein the adhesive is substantially free of a tackifier.

3. The hot melt adhesive composition of claim 1, wherein the second amorphous polymer comprises a viscous liquid with molecular weight of about 1,000-20,000 and a Saybolt Universal seconds (SUS) viscosity at 100° C. of about 100 to 20,000.

4. The hot melt adhesive composition of claim 1, wherein the second amorphous polymer comprises a polyisobutylene with a molecular weight of 1,500 to 6,000.

5. The hot melt adhesive composition of claim 1, wherein the density of the adhesive composition is less than 0.9 g-cm$^{-3}$.

6. The hot melt adhesive composition of claim 1, wherein the density of the adhesive composition is less than 0.87 g-cm$^{-3}$.

7. A disposable article comprising a substrate combined with a film, fiber, cellulose sheet or non-woven having an adhesive bond there between comprising the adhesive of claim 1.

8. A disposable diaper article comprising a substrate combined with a film, fiber, cellulose sheet or non-woven having an adhesive bond there between comprising the adhesive of claim 1.

9. The hot melt adhesive composition of claim 1, wherein the adhesive is substantially free of a tackifier.

10. The hot melt adhesive composition of claim 1, wherein the second amorphous polymer comprises a viscous liquid with molecular weight of about 1,000-20,000 and a Saybolt Universal seconds (SUS) viscosity at 100° C. of about 100 to 20,000.

11. The hot melt adhesive composition of claim 1, wherein the second amorphous polymer comprises a polyisobutylene with a molecular weight of 1,500 to 6,000.

12. The hot melt adhesive composition of claim 1, wherein the density of the adhesive is less than 0.9 g-cm$^{-3}$.

13. The hot melt adhesive composition of claim 1, wherein the density of the adhesive is less than 0.87 g-cm$^{-3}$.

14. A hot melt adhesive composition comprising:
    (i) about 90 wt. % to about 10 wt. % of an amorphous polyolefin composition comprising a copolymer having more than 40 mole % 1-butene, the copolymer having a viscosity of between 2000 and 8000 cps at a temperature of 190° C.; and
    (ii) about 0.1 wt. % to about 50 wt. % of a polyisobutylene;
    wherein the adhesive composition is substantially free of a tackifier;
    wherein the hot melt adhesive composition has a softening point temperature range of 115° C. to about 130° C.

15. The hot melt adhesive composition of claim 14, wherein the polyisobutylene has a molecular weight of about 2000 to 3000.

16. The hot melt adhesive composition of claim 14, wherein the density of the adhesive composition is less than 0.9 g-cm$^{-3}$.

17. The hot melt adhesive composition of claim 14, wherein the density of the adhesive composition is less than 0.87 g-cm$^{-3}$.

18. A disposable article comprising a substrate combined with a film, fiber, cellulose sheet or non-woven having an adhesive bond there between comprising the adhesive of claim 14.

19. A disposable diaper article comprising a substrate combined with a film, fiber, cellulose sheet or non-woven having an adhesive bond there between comprising the adhesive of claim 14.

20. A hot melt adhesive composition consisting essentially of:
  (i) a blend of amorphous polyolefin copolymers, each amorphous polyolefin copolymer comprising more than 40 mole % 1-butene, at least one amorphous polyolefin copolymer having a viscosity of between 2000 and 8000 cps at a temperature of 190° C.; and
  (ii) a second amorphous polymer comprising at least one butene monomer, the polymer having a molecular weight (MW) of at least 1000 wherein the polymer is compatible with the polyolefin.

21. A disposable article comprising a substrate combined with a film, fiber, cellulose sheet or non-woven having an adhesive bond there between comprising the adhesive of claim 20.

22. A disposable diaper article comprising a substrate combined with a film, fiber, cellulose sheet or non-woven having an adhesive bond there between comprising the adhesive of claim 20.

23. A hot melt adhesive composition consisting essentially of:
  (i) an amorphous polyolefin copolymer comprising more than 40 mole % 1-butene, the amorphous polyolefin copolymer having a viscosity of between 2000 and 8000 cps at a temperature of 190° C.; and
  (ii) a second amorphous polymer comprising at least one butene monomer, the second amorphous polymer having a molecular weight ($MW_n$) range of about 5,000 to about 45,000, wherein the second amorphous polymer is compatible with the amorphous polyolefin copolymer;
  wherein the hot melt adhesive composition has a softening point temperature range of 115° C. to about 130°.

* * * * *